(12) United States Patent
Kang

(10) Patent No.: US 11,071,874 B2
(45) Date of Patent: Jul. 27, 2021

(54) HYBRID PLASMA DEVICE FOR SKIN BEAUTY AND SKIN REGENERATION TREATMENTS

(71) Applicant: SHENB Co., Ltd., Seoul (KR)

(72) Inventor: Sun Young Kang, Seoul (KR)

(73) Assignee: SHENB Co., Ltd., Seoul (KR)

( * ) Notice: Subject to any disclaimer, the term of this patent is extended or adjusted under 35 U.S.C. 154(b) by 345 days.

(21) Appl. No.: 16/059,079

(22) Filed: Aug. 9, 2018

(65) Prior Publication Data

US 2019/0046809 A1 Feb. 14, 2019

(30) Foreign Application Priority Data

Aug. 10, 2017 (KR) .................. 10-2017-0101526

(51) Int. Cl.
*A61N 5/06* (2006.01)
*A61N 1/44* (2006.01)
(Continued)

(52) U.S. Cl.
CPC ............. *A61N 1/44* (2013.01); *A61N 5/0616* (2013.01); *H01J 37/32449* (2013.01); *H05H 1/46* (2013.01)

(58) Field of Classification Search
CPC .......... A61N 1/44; A61N 5/0616; A61N 7/00; A61N 2007/0034; A61N 1/0404;
(Continued)

(56) References Cited

U.S. PATENT DOCUMENTS

| 4,674,683 | A | * | 6/1987 | Fabel | ..................... B05B 7/226 219/121.38 |
| 7,862,564 | B2 | * | 1/2011 | Goble | .................. A61B 18/042 606/41 |

(Continued)

FOREIGN PATENT DOCUMENTS

| KR | 10-2003-0015084 A | 2/2003 |
| KR | 20-0325459 Y1 | 8/2003 |

(Continued)

OTHER PUBLICATIONS

"Reattachment and Apoptosis after plasma-needle treatment of cultured cells," Ingrid E. Kieft, IEEE transaction of plasma, vol. 34, No. 4, Aug. 2006.

(Continued)

*Primary Examiner* — Linda C Dvorak
*Assistant Examiner* — Nicholas S Borsch
(74) *Attorney, Agent, or Firm* — Patent Office of Dr. Chung Park

(57) ABSTRACT

A hybrid plasma device includes a power supply; a manipulation unit configured to receive at least two skin treatment programs; a gas supply unit configured to supply at least one inert gas; a control unit configured to control the gas supply unit to supply one species of inert gases or to supply at least two species of inert gases; a gas output unit configured to be controlled to output one species of inert gases or to output a mixture of at least two species of inert gases; a plasma handpiece configured to receive said one species of inert gases or the mixture of at least two species of inert gases from the gas output unit and to generate plasma from said one species or mixture to and to eject the generated plasma out of the handpiece; and a plasma driver unit configured to apply power to the plasma handpiece.

4 Claims, 5 Drawing Sheets

(51) Int. Cl.
　　*H01J 37/32*　　(2006.01)
　　*H05H 1/46*　　(2006.01)

(58) Field of Classification Search
　　CPC ....... A61N 1/06; H01J 37/32449; H05H 1/46;
　　　　　　　　　　　　　A61B 18/042; A61B 2018/00583
　　USPC .............. 219/121.5, 121.51, 121.52, 121.48,
　　　　　　　　219/121.39, 75; 315/111.21; 313/231.32,
　　　　　　　　　　　　　　　　　　　　　　313/231.51
　　See application file for complete search history.

(56) References Cited

U.S. PATENT DOCUMENTS

| | | | | |
|---|---|---|---|---|
| 2006/0009763 | A1* | 1/2006 | Goble ................. | A61B 18/042 606/49 |
| 2007/0156124 | A1* | 7/2007 | Ignon .................... | A61B 17/54 606/9 |
| 2011/0282340 | A1* | 11/2011 | Toth ................... | A61B 18/1492 606/33 |
| 2016/0331439 | A1* | 11/2016 | Winkelman ............. | A61K 8/22 |
| 2019/0090339 | A1* | 3/2019 | Frame .................. | A61L 2/0011 |

FOREIGN PATENT DOCUMENTS

| | | |
|---|---|---|
| KR | 2003-0080507 A | 10/2003 |
| KR | 20-0395359 Y1 | 9/2005 |
| KR | 10-1026945 B1 | 3/2011 |
| KR | 10-2012-0039199 A | 4/2012 |

OTHER PUBLICATIONS

"Floating electrode dielectric barrier discharge plasma in air promoting apoptotic behavior in melanoma skin cancer cell lines," Plasma chemistry and plasma processing , Apr. 2007, vol. 27, issue 2, pp. 163-176.
"Giant electric field induced reversible and permanent magnetization reorientation on magnetoelectric Ni," Appl, physics letter 98, 012504 (2011).
20th Symposium on Application of Plasma processes, Tatranska, Lomnica, Slovakia, Jan. 17-22, 2015.
"Floating electrode discharge barrier Discharge plasma in air promoting apoptotic behavior in melanoma skin cancer cell lines," plasma chemistry and plasma processing, Apr. 2007, vol. 27, issue 2, pp. 163-176.
"Giant electric-field-induced reversible and permanent magnetization reorientation on magnetoelectric Ni/(011) heterostructure," Applied Physics letter 98, 012504 (2011).
"20th Symposium on Application of Plasma Process," tatranska, Lominca, Slovakia, Jan. 17-22, 2015.
Heinlin, J et al, "Plasma medicine: Possible Application in Dermatology", JDDG, 2010, 8:968-976.
Murakami et al, "Chemical kinetics and reactive species in atmospheric pressure helium-oxygen plasmas with humid-air impurities", Plasma Sources Sci. Technol. 22 (2013) 015003 (29pp).
Sensenig et al, "Non-thermal Plasma Induces Apoptosis in Melanoma Cells via Production of Intracellular Reactive Oxygen Species", Annals of Biomedical Engineering, vol. 39, No. 2, Feb. 2011 (c 2010) pp. 674-687.
Stoffels et al, "Plasma needle for in vivo medical treatment: recent developments and perspectives", Plasma Sources Sci. Technol. 15 (2006) S169-S180.

* cited by examiner

[Figure 1]
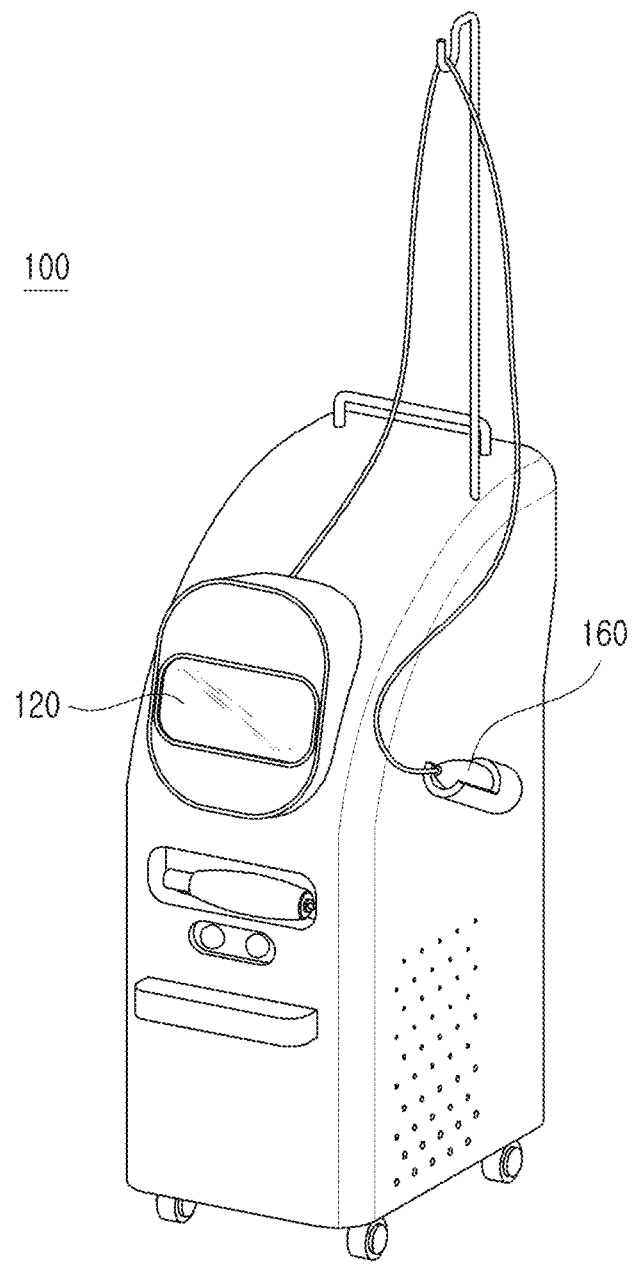

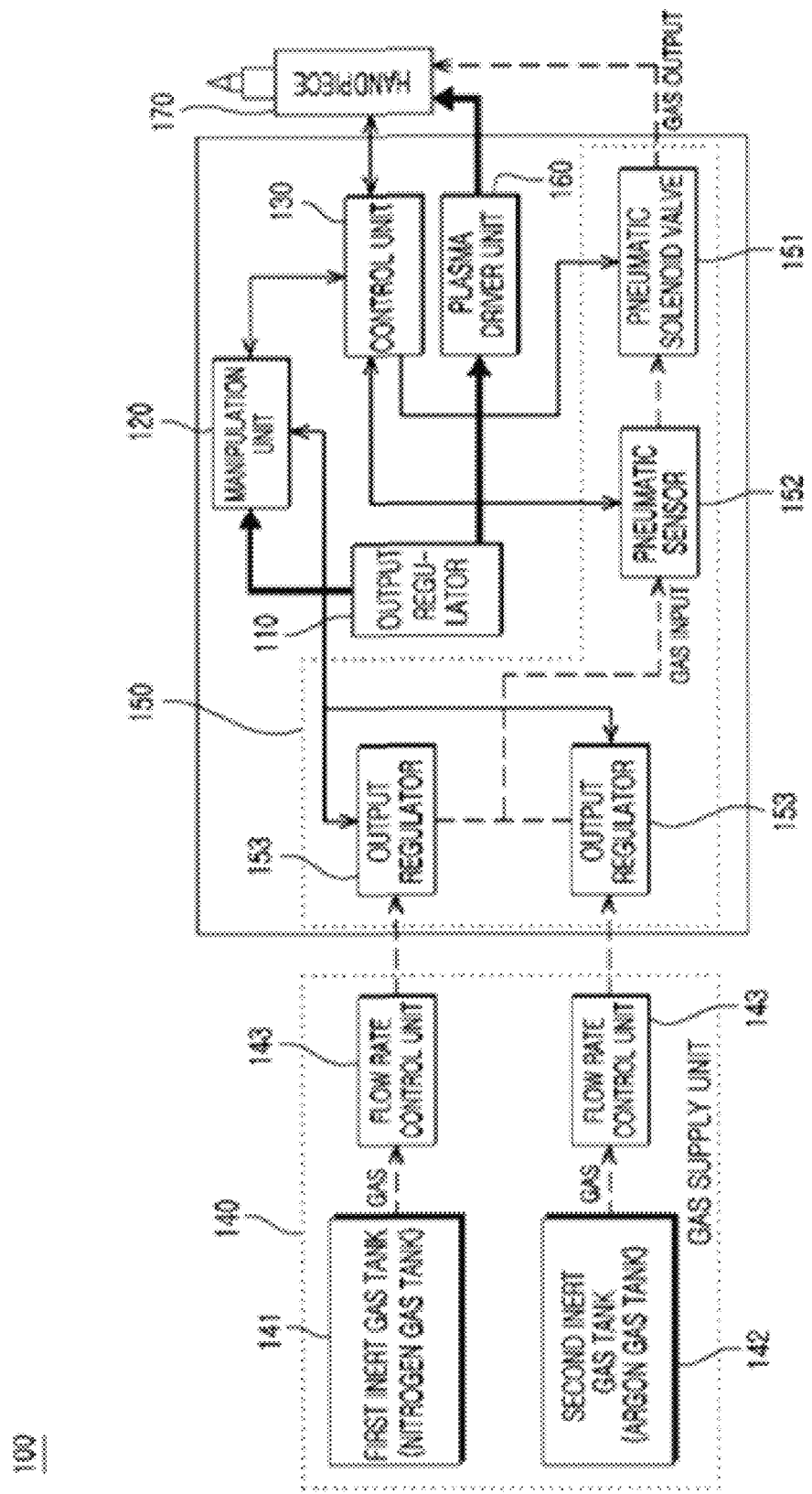
[Figure 2]

[Figure 3]
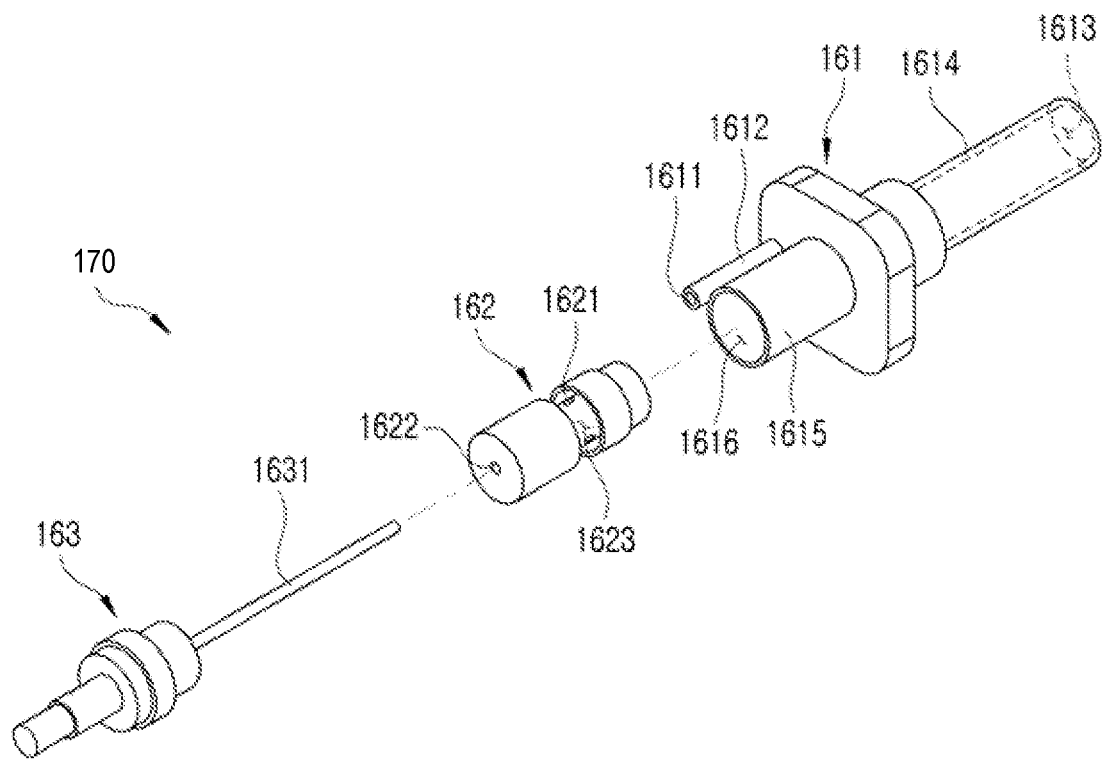
[Figure 4]
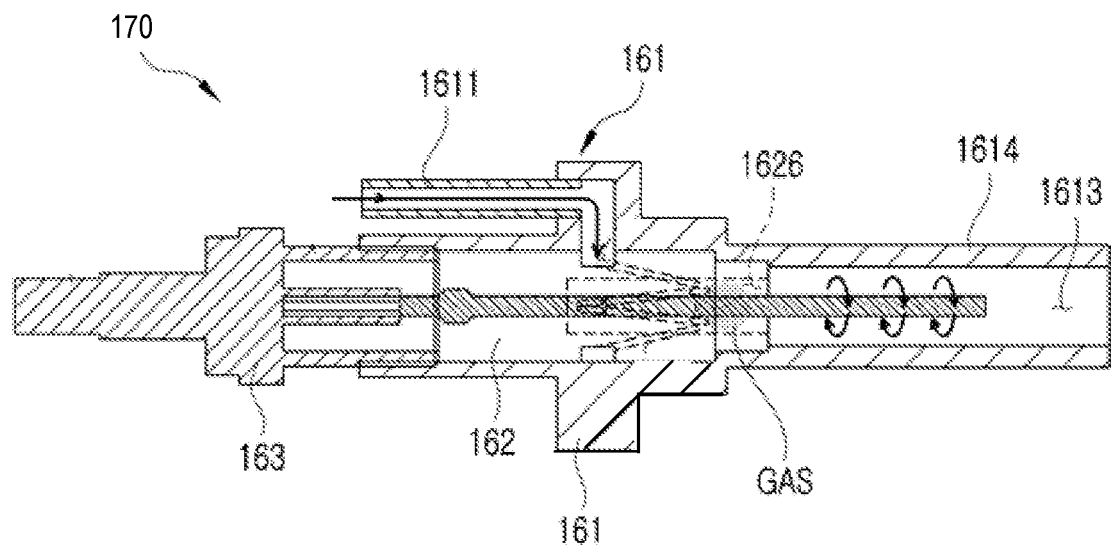

[Figure 5]
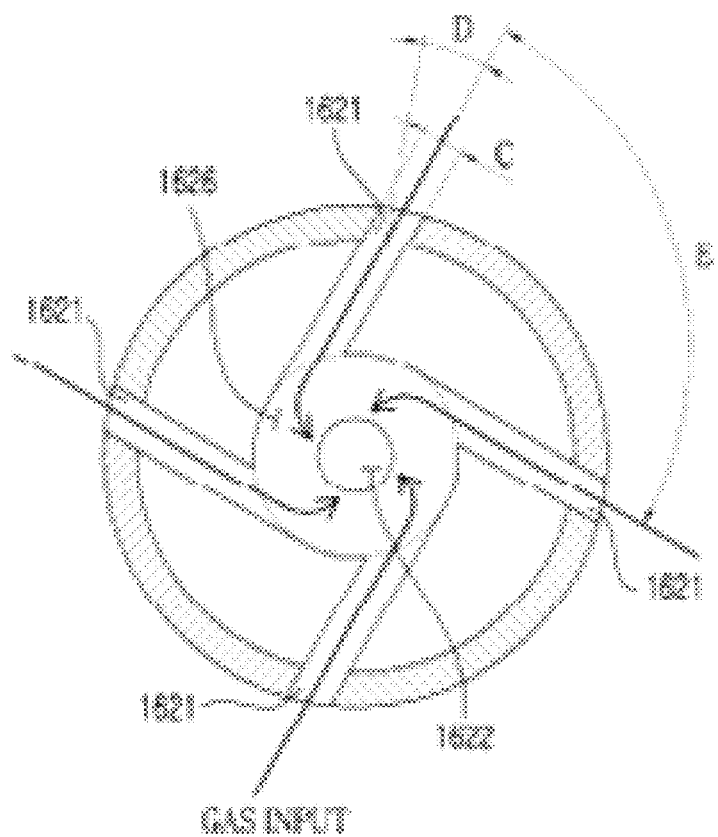
[Figure 6]
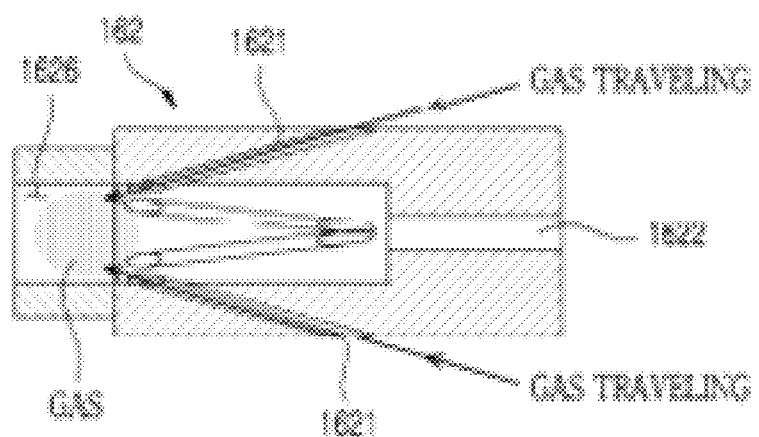

[Figure 7]

HYBRID PLASMA DEVICE FOR SKIN BEAUTY AND SKIN REGENERATION TREATMENTS

TECHNICAL FIELD

The present disclosure relates to a hybrid plasma device for skin beauty and skin regeneration treatments, and more particularly, to a hybrid plasma device for skin beauty and skin regeneration treatments to enable a skin regeneration treatment and a skin beauty treatment in a single device by mixing two or more species of inert gases.

RELATED ART

Conventionally, in a method for improving skin tissue aging, scars and the like, only medicines such as solutions, creams, gels, and ointments for a skin regeneration have been simply applied to the skin.

However, amounts of the solutions, creams, gels, ointments and the like which are absorbed into a dermis layer of the skin and effectively act on the skin were very small, compared to total amounts of the solutions, creams, gels and ointments applied to the skin.

A possibility that the applied solution passes through a skin layer of the skin is only 0.3% of a total content, and the remaining 99.7% does not pass through a sebum of an outermost skin and remains on the skin or may be dried up and disappeared.

Therefore, there has been a limit in improving a wrinkle or imparting elasticity to the skin using the applied solution. As a result, there has been a problem in that the treatment for improving the tissue of the skin is not efficiently performed.

Accordingly, methods for dramatically increasing the absorption rates of the solutions, creams, gels, and ointments in the skin layer in order to regenerate the skin tissue effectively is to use an electrical stimulation, a cold/hot stimulation or a mechanical stimulation, for example, a needle treatment are being implemented.

Accordingly, a skin beauty device for conveniently performing the above-described methods has been developed. Generally, the skin beauty device has been used by developing a device that manages the skin by applying negative pressure, ultrasonic waves, a high-frequency heating to the skin and the like, or stimulates the skin using steam, an anion, the cold/hot stimulation, a stimulation with vibration and the like.

Further, for example, as described in Korean Patent Laid-Open Publication No. 2003-0080507, a skin beauty device capable of treating the skin by mixing two or more of the above-described methods in a single device has been developed and used.

In addition, a skin treatment device (Utility Model Registration No. 395359, titled a microneedle roller) suitable for restorative treatment by stimulating the skin or forming a micro channel in the skin tissue, nutrients such as vitamin C and peptide are effectively supplied to the dermal layer including collagen to improve stretch marks and wrinkles, as well as to improve acne scars and burn scars is disclosed.

However, since the above technique relies only on the skin stimulation effect by the micro needle, the effect of softening the skin surface and softening the scar tissue may be expected, but the effect of improving the wrinkle by promoting the regeneration of the collagen in a human body was unsatisfactory.

Further, in the case of the skin beauty device capable of the cold/hot massage, there is a skin beauty device for both cold and hot massages using a thermoelement. The skin beauty device uses a method for cooling the thermoelement by dissipating a heat generated from the thermoelement by closely attaching a heat sink to a back face of the thermoelement.

For example, power is supplied to the thermoelement to generate cold air on a front face of the thermoelement to perform the cold massage. At this time, since hot air is generated from the back face of the thermoelement, the thermoelement must be cooled. This is because the temperature of the hot air generated from the back face of the thermoelement continuously rises, and the heat affects the front face of the thermoelement. That is, because the hot air generated from the back face of the thermoelement increases the temperature of the cold air generated from the front face of the thermoelement, and thus the cold massage effect is lowered.

As described above, there is a difficulty in switching between the temperature of the cold air and the temperature of the hot air, so that a cooling fan is provided to solve this problem, but the skin beauty device becomes bulky.

In addition, a skin care method using oxygen for a skin cell activation is well known. Thus, a vacuum swing adsorption type oxygen generator (utility model registration No. 325459), a skin beauty device, which is closely contacted with an epidermis and massaging the epidermis by sucking while supplying the oxygen and the nutrients is disclosed.

This oxygen generator is for driving an oscillating piston type (or oscillating diaphragm type) oxygen vacuum pump and an oscillating piston type (or oscillating diaphragm type) nitrogen vacuum pump for sucking and exhausting oxygen and nitrogen respectively by a single motor in the oxygen generator. However, the technique has a problem that a noise and vibration are severe.

In addition, a skin beauty device using ultrasonic waves has been used by developing a technique of skin and obesity managements by stimulating a skin cell by regular vibration of the ultrasonic waves to remove wastes and massage the skin.

However, in order to maximize the effect of the ultrasonic wave, the skin beauty device using the ultrasonic waves uses ultrasonic waves of 20 KHz to 80 KHz, which causes serious noise when user receives the skin treatment.

In general, a sound from 20 Hz to 16,000 Hz (16 kHz) can be heard by human being. However, there is a problem that a sound above 20 KHz, that is, the ultrasonic wave may be exceptionally recognized by people. Further, there is a side effect that a massaging part directly contacted with the skin is formed of a metal material so that allergies or troubles are caused during long-time use.

Meanwhile, plasma, also referred to as the fourth state of matter, means that molecules contained in the gas collide with each other to cause some of outermost electrons to fall, thereby forming an ionized gas in which a cation and an anion are mixed.

The plasma is divided into a high temperature plasma and a low temperature plasma depending on a temperature characteristic. Among these, the low temperature plasma is characterized in that hydrogen peroxide vapor with strong penetration power is produced. Recently, a sterilizer using the low temperature plasma has been used for a sterilization of medical instruments and the like.

In this connection, when the low temperature plasma is brought into contact with a patient's skin, it is known that there is a skin cell regeneration effect along with the sterilization effect. In the Netherlands, Eva Stoffels reported killing effects of the plasma on various mammalian cells including cancer cells and on microorganisms using a syringe type plasma in the 2000s [Stoffels, Plasma Sources Sci Technol 15, 2006].

The plasma may act directly to the cell, but there is a report that active species generated by the plasma induce necrosis or apoptosis of the cancer cell to kill the cell [Murakami, Plasma Sources Sci Technol 22, 2013; Sensenig, Ann Biomed Eng 39, 2011].

Various active species generated by the plasma have a strong sterilizing effect and destroy a cell wall of a bacteria. Interestingly, a living tissue undergoes almost no injury under the same conditions.

That is, the generated active species releases hydroxyl groups (OH radicals), ions, electrons, photons, ionized gas, and small amount of UV and the like, which are harmless to the human body. In addition, OH is known to act a very important role in a bacterial disinfection [Kang, Appl Phys Lett 98, 2011].

A plasma treatment after the tissue injury showed that it was effective in preventing a secondary infection of the tissue and healing a wound due to its sterilization action and fast hemostatic action respectively. That is, repeated plasma treatment for 2 minutes per day showed an excellent wound healing effect, and after repeated plasma treatment for 11 times, there were no bacteria in the wound area [Gregory, Plasma Chem Plasma Process 26, 2006].

A periodic plasma treatment to the skin stimulates the skin cells to increase the collagen of the dermis layer and because of increased secretion of VEGF a new blood vessel provides nutrients to the skin cells therefore antiaging effects may be expected.

Thus, the plasma may be very useful for the wound healing of not only general patients but also blood diseases patients [Heilin, J Dtsch Dermatol Ges 8, 2010].

In the skin disease device using the low temperature plasma, Patent No. 10-1212749 has developed a device having a contact protrusion structure which contacts with the skin to apply a minute current and generating a hydroxyl group by simultaneously supplied water. However, supplying the water separately is inconvenient and complicated. Patent No. 10-1026945 is composed of a device for generating ozone gas through a low temperature plasma generator and recovering the ozone gas immediately after contact with the skin to decompose the ozone, resulting in a complicated structure and a large volume.

SUMMARY

This Summary is provided to introduce a selection of concepts in a simplified form that are further described below in the Detailed Description. This Summary is not intended to identify all key features or essential features of the claimed subject matter, nor is it intended to be used alone as an aid in determining the scope of the claimed subject matter.

A purpose of the present disclosure is to provide a hybrid plasma device for skin beauty and skin regeneration treatments enable a skin regeneration treatment and a skin beauty treatment by mixing two or more species of inert gases.

Another purpose of the present disclosure is to provide a hybrid plasma device for skin beauty and skin regeneration treatments which guides an input path of an inert gas to a plasma handpiece to an output direction of the plasma, and the inert gas is output in the form of a vortex flow from an end of the output portion.

In one aspect of the present disclosure, there is provided a hybrid plasma device for skin beauty and skin regeneration treatments of the present disclosure, the device including: a power supply configured to supply power; a manipulation unit configured to receive at least two skin treatment programs among a plurality of skin treatment programs; a gas supply unit configured to supply at least one inert gas; a control unit configured to control the gas supply unit, based on the skin treatment program input from the manipulation unit, to supply one species of inert gases or to supply at least two species of inert gases; a gas output unit configured to be controlled by the control unit to output one species of inert gases or to output a mixture of at least two species of inert gases based on the skin treatment program input from the manipulation unit; a plasma handpiece configured to receive said one species of inert gases or the mixture of at least two species of inert gases from the gas output unit and to generate plasma from said one species or mixture to and to eject the generated plasma out of the handpiece; and a plasma driver unit configured to apply power to the plasma handpiece.

In one embodiment of the hybrid plasma device for skin beauty and skin regeneration treatments, the gas supply unit includes: a first inert gas tank configured to supply nitrogen; and a second inert gas tank configured to supply argon.

In one embodiment of the hybrid plasma device for skin beauty and skin regeneration treatments, the gas output unit includes: output regulators configured to mix two or more species of the inert gases supplied from the gas supply unit; a pneumatic sensor configured to sense a pressure state of the mixed inert gas from the output regulators; and a pneumatic solenoid valve configured to regulate a pressure of the inert gas output to the plasma handpiece based on the skin treatment program input from the manipulation unit, the control unit is configured to control the gas output unit, based on the skin treatment program input from the manipulation unit, to output one species of the inert gases or a mixture of two or more species of the inert gases to the plasma handpiece.

In one embodiment of the hybrid plasma device for skin beauty and skin regeneration treatments, the plasma handpiece includes: a plasma output nozzle including: a gas input portion to receive the inert gas, a guide receiving a gas output guide therein, and a nozzle configured to output plasma entered therein, wherein the plasma is generated via applying a voltage to the inert gas; a gas output guide including: an elongate electrode rod receiving channel defined therein, a plurality of vortex input channels defined therein, and a gas converging space defined therein, wherein the elongate electrode rod receiving channel extends across an entire length of the gas output guide, wherein the vortex input channels extends in different directions toward the gas converging space, such that the inert gas enters the vortex input channels to generate a vortex flow in the gas converging space and to output the vortex flow toward the nozzle; and an electrode rod assembly having an elongate electrode rod, where the electrode rod is inserted into the elongate electrode rod receiving channel such that a portion of the rod is disposed in the nozzle.

In one embodiment of the hybrid plasma device for skin beauty and skin regeneration treatments, the inert gas is input from the gas input portion, wherein the vortex input channels are formed in an oblique direction of 15° to 25° with respect to a longitudinal direction of the electrode rod.

In one embodiment of the hybrid plasma device for skin beauty and skin regeneration treatments, four vortex input channels are formed in an outer periphery of the gas output guide, wherein adjacent vortex input channels are spaced apart from each other by an interval of 90 degrees.

In one embodiment of the hybrid plasma device for skin beauty and skin regeneration treatments, the inert gas is output in a vortex flow along the longitudinal direction of the electrode rod disposed in the nozzle and around an outer face of the electrode rod.

In one embodiment of the hybrid plasma device for skin beauty and skin regeneration treatments, the plurality of skin treatment programs includes a skin beauty treatment program and a skin regeneration treatment program, wherein a mixture ratio of the inert gases for the skin beauty treatment program is different from a mixture ratio of the inert gases for the skin regeneration treatment program.

The hybrid plasma device for the skin beauty and skin regeneration treatments according to the present disclosure may mix various inert gases and adjust the mixing ratio of the mixed inert gas, thus various skin regeneration and skin beauty treatments may be performed simultaneously and in combination such that user convenience may be maximized.

The present disclosure may also treat various skin diseases by adjusting the mixing ratio of the various inert gases at a rate that maximizes the therapeutic effect, thus patients with various skin disease may be treated.

Therefore, the plasma handpiece of the present disclosure induces the traveling path of the gas to the gas converging space defined in the plasma output hole, which is arranged the discharging direction of the gas. Thus, the gas vortex is generated at an outer side of the electrode rod such that the plasma is accurately gathered at the treatment area. Therefore, the skin regeneration effect may be maximized in the skin regeneration treatment.

In addition, the hybrid plasma device for the skin regeneration and skin beauty treatments induces a direct cell activation (including a muscle cell) and a skin tissue regeneration. Further, the plasma device has excellent repair regeneration effect that repairs the tissue in the state of the tissue being removed.

BRIEF DESCRIPTION OF THE DRAWINGS

FIG. 1 is a perspective view of a hybrid plasma device for skin beauty and skin regeneration treatments.

FIG. 2 is a block diagram of a hybrid plasma device for skin beauty and skin regeneration treatments.

FIG. 3 is an exploded perspective view of a plasma handpiece.

FIG. 4 is a sectional view of a plasma handpiece.

FIG. 5 is a cross-sectional view for illustrating a vortex input channel in a gas output guide.

FIG. 6 is a cross-sectional view for illustrating a gas entering structure of a vortex input channel in a gas output guide.

FIG. 7 is a diagram of GUI screen showing various available treatments based on various skin beauty and skin regeneration treatment programs.

DETAILED DESCRIPTION

For simplicity and clarity of illustration, elements in the figures are not necessarily drawn to scale. The same reference numbers in different figures denote the same or similar elements, and as such perform similar functionality. Also, descriptions and details of well-known steps and elements are omitted for simplicity of the description. Furthermore, in the following detailed description of the present disclosure, numerous specific details are set forth in order to provide a thorough understanding of the present disclosure. However, it will be understood that the present disclosure may be practiced without these specific details. In other instances, well-known methods, procedures, components, and circuits have not been described in detail so as not to unnecessarily obscure aspects of the present disclosure.

Examples of various embodiments are illustrated and described further below. It will be understood that the description herein is not intended to limit the claims to the specific embodiments described. On the contrary, it is intended to cover alternatives, modifications, and equivalents as may be included within the spirit and scope of the present disclosure as defined by the appended claims.

It will be understood that, although the terms "first", "second", "third", and so on may be used herein to describe various elements, components, regions, layers and/or sections, these elements, components, regions, layers and/or sections should not be limited by these terms. These terms are used to distinguish one element, component, region, layer or section from another element, component, region, layer or section. Thus, a first element, component, region, layer or section described below could be termed a second element, component, region, layer or section, without departing from the spirit and scope of the present disclosure.

The terminology used herein is for the purpose of describing particular embodiments only and is not intended to be limiting of the present disclosure. As used herein, the singular forms "a" and "an" are intended to include the plural forms as well, unless the context clearly indicates otherwise. It will be further understood that the terms "comprises", "comprising", "includes", and "including" when used in this specification, specify the presence of the stated features, integers, operations, elements, and/or components, but do not preclude the presence or addition of one or more other features, integers, operations, elements, components, and/or portions thereof. As used herein, the term "and/or" includes any and all combinations of one or more of the associated listed items. Expression such as "at least one of" when preceding a list of elements may modify the entire list of elements and may not modify the individual elements of the list.

Spatially relative terms, such as "beneath," "below," "lower," "under," "above," "upper," and the like, may be used herein for ease of explanation to describe one element or feature's relationship to another element s or feature s as illustrated in the figures. It will be understood that the spatially relative terms are intended to encompass different orientations of the device in use or in operation, in addition to the orientation depicted in the figures. For example, if the device in the figures is turned over, elements described as "below" or "beneath" or "under" other elements or features would then be oriented "above" the other elements or features. Thus, the example terms "below" and "under" can encompass both an orientation of above and below. The device may be otherwise oriented for example, rotated 90 degrees or at other orientations, and the spatially relative descriptors used herein should be interpreted accordingly.

Unless otherwise defined, all terms including technical and scientific terms used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

In the following description, numerous specific details are set forth in order to provide a thorough understanding of the present disclosure. The present disclosure may be practiced without some or all of these specific details. In other instances, well-known process structures and/or processes have not been described in detail in order not to unnecessarily obscure the present disclosure.

A hybrid plasma device 100 for skin beauty and skin regeneration treatments of the present disclosure may effectively induce a cell activation, a cell migration to a wound area, a cell proliferation and a cell differentiation during skin beauty and skin regeneration treatments. Therefore, the device 100 may be useful for treatments of skin damage, skin related diseases and the skin beauty.

In the present disclosure, the skin regeneration and skin beauty treatments may be adjusted by plasma exposure conditions such as amount of plasma gas emission, distance from a plasma source to an affected area, the number of plasma exposure, plasma exposure time and the like.

The "skin regeneration" of the present disclosure may include any damage of a muscle tissue. A muscle damage may result from a physical trauma to the muscle tissue due to an accident, a sports injury, an endocrine disorder, a disease, wound or a surgical operation.

Further, the "skin regeneration" of the present disclosure may also effectively control or eliminate *Staphylococcus aureus*, a major cause of atopic dermatitis.

The plasma device 100 for skin regeneration and skin beauty treatments of the present disclosure has at least one skin beauty and skin regeneration effect selected from the group consisting of a sterilization treatment, a smooth water supplying using a hydrophilicity of the plasma, the activation of the cell, the cell migration to the wound area, the cell proliferation and the cell differentiation.

Thus, the plasma device 100 for the skin regeneration and skin beauty treatments induces a direct cell activation (including a muscle cell) and a skin tissue regeneration. Further, the plasma device 100 has excellent repair regeneration effect that repairs the tissue in the state of the tissue being removed.

Therefore, plasma device 100 for the skin regeneration and skin beauty treatments of the present disclosure may be effectively used for a treatment of the skin tissue and for a treatment of a patient suffering from a skin damage due to apoptosis, and the like or a skin damage-related disease. The treatments of the present disclosure include all of prophylactic, palliative and curing treatments.

Referring to FIG. 1 and FIG. 2, a hybrid plasma device for skin beauty and skin regeneration treatments according to an embodiment of the present disclosure will be described. FIG. 1 is a perspective view of a hybrid plasma device for skin beauty and skin regeneration treatments and FIG. 2 is a block diagram of a hybrid plasma device for skin beauty and skin regeneration treatments.

The hybrid plasma device 100 for skin beauty and skin regeneration treatments according to the present disclosure includes a power supply 110, a manipulation unit 120, a control unit 130, a gas supply unit 140, a gas output unit 150, a plasma driver unit 160, and a plasma and a handpiece 170.

In the hybrid plasma device 100 of the present disclosure, on the front surface of a main body, a manipulation unit 120 is arranged for user to input various skin beauty and skin regeneration treatment programs thereto. The manipulation unit 120 includes an LCD touch screen type display. A plasma driver unit 160 is disposed on a side face of the main body. The plasma driver unit 160 has a size and shape such that the unit 160 is be held and moved by the user with one hand. A first inert gas tank 141 for supplying nitrogen and a second inert gas tank 142 for supplying argon are disposed inside the main body.

In addition, a portable plasma generator may be disposed on the front surface of the main body so as to be attachable and detachable. The portable plasma generator generates a low temperature plasma (cold plasma) irradiated toward the skin and is operated by a DC voltage.

Meanwhile, the power supply 110 is a power supply for supplying power to the hybrid plasma device 100 for the skin beauty and skin regeneration treatments according to the present disclosure.

The power supply 110 receives an available voltage from an external source. The power supply 110 may be supplied with a commercial voltage of 110 V or 220 V, or may be supplied with power from a detachable built-in type battery, or may be supplied with a USB cable connected to a laptop, and the like.

The power supply 110 receives the external power and the internal power under the control of the control unit 130 and supplies power to respective components.

The manipulation unit 120 may be the LCD touch screen type in which a user may input the various skin beauty and skin regeneration treatment programs, and various types of input devices may be used as long as UI display and menu input are possible. When the user enables inputting a menu via UI display of the unit 120, the user may use various kinds of input devices. The user may select a skin treatment program for the skin beauty and skin regeneration treatment such as an atopy treatment, a wrinkle treatment, a scar treatment, a burn treatment, etc. via the manipulation unit 120.

The manipulation unit 120 senses a touch (or touch input) applied onto the touch screen using at least one of various touch methods such as a resistive film type, a capacitive type, an infrared type, an ultrasonic type, and a magnetic field type. In this connection, a touch object may be, for example, a finger, a touch pen or a stylus pen, a pointer, and the like.

The manipulation unit 120 may function as a user input unit for providing a user input interface, and simultaneously may also provide an output interface.

In addition to the operations related to the application program, the control unit 130 typically controls overall operations of each of components. The control unit 130 may provide or process information or functions appropriate for the user by processing signals, data, information, etc. input or output through the components or by driving application programs stored in a memory (not shown).

The control unit 130 may also control at least some of the components of FIG. 2 to drive a program stored in the memory (not shown). As described above, the control unit 130 processes the data or the information corresponding to the touch input through the manipulation unit 120, and further outputs visual information corresponding to the processed data to the manipulation unit 120.

The control unit 130 includes, for example, an operating system based on WINDOWS CE. The control unit 130 controls the flow rate control unit 143, monitors the pneumatic sensor 152, and controls separately the output regulators 153 and controls the pneumatic solenoid valve 151 to control the supply amount and mixing amount of the inert gas.

That is, when the various skin beauty and skin regeneration treatment programs are selected through the manipulation unit 120, for example, when the user select the skin regeneration treatment program and select one treatment of the atopy treatment, wrinkle treatment, scar treatment and burn treatment of the skin regeneration treatment program thereof, the control unit 130 controls the output regulator 153, the pneumatic solenoid valve 151 and the like based on the selected skin treatment program in order to mix the nitrogen gas, which is the first inert gas with the argon gas, which is the second inert gas.

In this connection, when using only the nitrogen gas for the atopy treatment, the control unit 130 controls each component to output plasma by using only the nitrogen gas. In addition, in case when the nitrogen gas and argon gas need to be mixed and output in the selected skin treatment program, the control unit 130 also controls each component to mix the two species of gases.

In this connection, the mixing amount of the nitrogen gas and the argon gas is stored in the memory (not shown) based on each skin treatment program, and various skin treatment programs may be continuously updated. Mixing ratio of the gases may also be adjusted by doctor, who is the user based on each skin treatment program.

The gas supply unit 140 includes the first inert gas tank 141 for supplying the nitrogen, the second inert gas tank 142 for supplying the argon, and the flow rate control units 143 connected to the respective gas tanks.

The flow rate control units 143 regulates outputs of the respective gases discharged from the respective tanks to for example 3 bar or less through each analogue output regulator. The flow rate control units 143 preferably use the analogue output regulator, but may also use a digital output regulator.

The gas output unit 150 includes the pneumatic solenoid valve 151, the pneumatic sensor 152, and the output regulators 153.

The pneumatic solenoid valve 151 may be embodied as a digital solenoid valve as controlled by the control unit 130 such that, in response to the skin treatment program input from the manipulation unit 120, the nitrogen gas stored in the first inert gas tank 141 is output, or the argon gas stored in the second inert gas tank 142 is output, or the nitrogen gas and the argon gas are mixed and output based on the selected skin treatment program.

The pneumatic sensor 152 is a pressure sensor for sensing a pressure of the gas output from each of the output regulators 153 to the pneumatic solenoid valve 151.

The output regulators 153 secondarily control the output of the nitrogen gas and the argon gas output through the respective flow rate control units 143 connected to the first inert gas tank 141 and the second inert gas tank 142, respectively.

Although the output regulator 153 is preferably a digital regulator, the present disclosure is not limited thereto. Based on a skin treatment program selected by the user, the control unit 130 controls the output regulators 153 to regulate the mixing ratio of inert gases or to select the single gas use.

The plasma driver unit 160 is an inverter type high efficiency power generator for applying a high voltage to an electrode rod 1631 disposed in a plasma handpiece 170 to be described later for plasma discharge.

A free bolt may be applied to the plasma driver unit 160. The unit 16 may then configure an inverter type power generator with 4 kV, 250 mA by changing the input power thereto to DC form and then applying 30 kHz voltage switching to the DC input. Conventional equipment receives 60 Hz power from a power transformer and boosts this voltage. Thus, an end output stage thereof has a large ripple due to the low switching frequency. However, the plasma driver unit 160 of the present invention significantly reduces the ripple using the high voltage switching. As a result, the life of a load component connected to the output stage thereof is lengthened, and accurate output control, fast feedback, and high efficiency output are achieved.

The plasma handpiece 170 is a plasma generating device that generates the plasma by discharging an arc using the nitrogen gas and the argon gas supplied from the first inert gas tank 141 and the second inert gas tank 142, respectively.

A more detailed description of the plasma handpiece 170 will be described below with reference to FIG. 3 to FIG. 6.

FIG. 3 is an exploded perspective view of the plasma handpiece. FIG. 4 is a sectional view of the plasma handpiece. FIG. 5 is a cross-sectional view for illustrating a vortex input channel in a gas output guide. FIG. 6 is a cross-sectional view for illustrating a gas entering structure of a vortex input channel in a gas output guide.

Preferably, the plasma handpiece 170 is configured to have a good grip feeling when the user is using and have a mechanical flexibility to treat a local area of various states.

In addition, the plasma handpiece 170 of the present disclosure may adjust physical properties of the plasma such as electron and ion densities, activated atoms or molecules, electric fields, induced magnetic fields, delivering energy and the like depending on type, size, material of the component generating the plasma, type and pressure of the gas used. Thus, there is also an advantage that selectivity and efficiency of the treatment may be enhanced based on the treatment area.

The plasma handpiece 170 includes a plasma output nozzle 161, a gas output guide 162, and an electrode rod assembly 163.

The plasma output nozzle 161 includes a gas input hole 1611, a gas input portion 1612, a plasma output hole 1613, a nozzle 1614, a guide 1615, and a connecting opening 1616.

The gas input portion 1612 is formed on one side of the plasma output nozzle 161 and is formed to face the opposite side of the nozzle 1614 so as to be supplied with the mixture of the nitrogen gas and the argon gas or the single nitrogen gas or the single argon gas through the above-mentioned output regulators 153.

The gas input portion 1612 is connected to the pneumatic solenoid valve 151 and is connected to a flexible gas supply line (flexible hose, tube and the like of various materials). The gas mixed with the nitrogen and the argon (hereinafter, gas mixed with the nitrogen and the argon is referred to as a mixed gas) is input through the gas input hole 1611.

The plasma output hole 1613 is defined in one side of the nozzle 1614 through which a plasma generated by arc discharging the single nitrogen gas or the single argon gas or the mixed gas input through the gas input portion 1612.

A guide 1615 is formed on the other side of the nozzle 1614, and a circular connecting opening 1616 to which a gas output guide 162 to be described later is coupled is defined in the guide 1615. A protruding portion formed on one side of the gas output guide 162 is inserted and coupled to the inside of the connecting opening 1616.

The gas output guide 162 includes a vortex input channel 1621, an elongate electrode rod receiving channel 1622, and a gas input space 1623.

The vortex input channel 1621 is configured to be connected to the gas input portion 1612 when the gas output guide 162 is coupled to the guide 1615.

Four vortex input channels 1621 are formed in the gas input space 1623 and spaced apart from each other by a predetermined interval such that the nitrogen gas, the argon gas, and the mixed gas input through the gas input portion 1612 are input in four directions.

In addition, the four vortex input channels 1621 are formed to be spaced apart from each other by a predetermined angle E, and for example the predetermined angle E is preferably 90 degrees.

The vortex input channel 1621 is formed to simultaneously input gas in an oblique direction and is formed at an angle of, for example, 19.4 degrees with respect to a longitudinal direction of the electrode rod 1631 disposed through an elongate electrode rod receiving channel 1622 to be described later.

That is, the vortex input channel 1621 is configured to input the gas input through the gas input portion 1612 in a substantially horizontal direction.

The handpiece structure of the conventional gas plasma was formed such that the traveling path of the gas and the input/output path of the gas were formed perpendicular to each other, thus the traveling path of each gas molecule was irregular. As a result, there was a problem that the gas was not discharged adjacent to the electrode rod and the electrode.

Therefore, the plasma handpiece 170 of the present disclosure induces the traveling path of the gas to the gas converging space 1626 in the plasma output hole 1613, which is arranged the discharging direction of the gas. Thus, the gas vortex is generated based on the electrode rod 1631, and then, the gas vortex is output to the plasma output hole 1613 due to an output pressure of the gas.

Therefore, in the present disclosure, the vortex input channel 1621 is configured to uniformly mix the nitrogen gas and the argon gas and the gas to be output to the nozzle 1614 is easily collected around the electrode rod 1631 such that the generated plasma is accurately gathered at the treatment area.

FIG. 7 is a diagram of GUI screen showing various available treatments based on various skin beauty and skin regeneration treatment programs.

This is the GUI screen of the manipulation unit 120 of the hybrid plasma device 100 for the skin beauty and skin regeneration according to the present disclosure.

Using the present disclosure's manipulation unit 120, the user may select various skin beauty and skin regeneration treatment programs. For example, the user selects a skin regeneration treatment program, and, then, the user may select the desired skin treatment program such as atopy treatment, wrinkle treatment, scar treatment or burn treatment, from the selected skin regeneration treatment program. When the user has selected the skin regeneration treatment program, the present device may apply the selected skin beauty treatment program to the patient.

That is, a conventional plasma device for skin beauty was used only for skin beauty using a single gas.

Previously, there was an inconvenient problem that a dermatologist needed to replace a gas or use another plasma device for therapeutic use after using the plasma device for skin beauty.

The hybrid plasma device 100 for the skin beauty and skin regeneration treatments according to the present disclosure has an advantage that the skin beauty and skin regeneration treatment programs may be used simultaneously in a single device.

In addition, it is possible to control various mixing ratios of the various gases (argon gas, nitrogen gas) depending on a type of the skin treatments (regeneration, skin beauty), for example, the atopic treatment, wrinkle treatment, scar treatment, skin regeneration treatment, thus, the skin beauty and skin regeneration treatments may maximize the therapeutic effect. Further, when only a single device is provided, the skin beauty and skin regeneration treatments are possible to performed at the same time, therefore a convenience of doctor, who is the user is improved.

What is claimed is:

1. A hybrid plasma device for skin beauty and skin regeneration treatments, the device comprising:
   a power supply configured to supply power;
   a manipulation unit configured to receive at least two skin treatment programs among a plurality of skin treatment programs;
   a gas supply unit configured to supply at least one inert gas;
   a control unit configured to control the gas supply unit, based on the at least two skin treatment programs, to supply one species of inert gas or to supply at least two species of inert gases;
   a gas output unit configured to be controlled by the control unit to output one species of inert gas or to output a mixture of at least two species of inert gases based on the at least two skin treatment programs;
   a plasma handpiece configured to generate plasma from the one species of inert gas or the mixture of at least two species of inert gases output from the gas output unit and to eject the plasma out of the plasma handpiece; and
   a plasma driver unit configured to apply power to the plasma handpiece;
   wherein the plasma handpiece includes:
   a plasma output nozzle including:
      a gas input portion for receiving the one species of inert gas or the mixture of at least two species of inert gases output from the gas output unit,
      a guide for receiving a gas output guide therein, the guide having a shape of a circular tube,
      a nozzle configured to output the plasma, wherein the plasma is generated via applying a voltage to the one species of inert gas or the mixture of at least two species of inert gases output from the gas output unit;
   the gas output guide including:
      an elongate electrode rod receiving channel defined therein,
      a plurality of vortex input channels defined therein, and
      a gas converging space defined therein; and
   an electrode rod assembly having only one elongate electrode rod, wherein the voltage is applied by the only one elongate electrode rod to generate the plasma,
   wherein the elongate electrode rod receiving channel extends across an entire length of the gas output guide, wherein the plurality of vortex input channels extends in different directions toward the gas converging space, such that inert gas enters the plurality of vortex input channels to generate a vortex flow in the gas converging space and to output the vortex flow toward the nozzle and wherein the elongate electrode rod is inserted into the elongate electrode rod receiving channel such that a portion of the elongate electrode rod is disposed in the nozzle,
   wherein the inert gas entering the plurality of vortex input channels is input from the gas input portion, wherein the plurality of vortex input channels are formed in an oblique direction of 15° to 25° with respect to a longitudinal direction of the elongate electrode rod,
   wherein the plurality of vortex input channels includes four vortex input channels formed in an outer periphery of the gas output guide, wherein two adjacent vortex input channels of the four vortex input channels are spaced apart from each other by an interval of 90 degrees, wherein an inert gas entered through the plurality of vortex input channels is output in a vortex flow along a longitudinal direction of the elongate electrode rod disposed in the nozzle and around an outer face of the elongate electrode rod, wherein the plasma output nozzle, the gas output guide, and the electrode rod assembly are separately formed and are configured to be assembled with each other, and when the plasma output nozzle, the gas output guide, and the electrode rod assembly are assembled with each other, the gas output guide is first inserted into a circular connecting opening of the plasma output nozzle, and then, the electrode rod assembly is coupled to a front end of the guide of the plasma output nozzle, wherein the elongate electrode rod of the electrode rod assembly passes through the gas output guide and the gas converging space and extends toward an output end of the plasma output hole, and wherein the elongate electrode rod of the electrode rod assembly has a first portion that extends from a downstream end of the gas converging space to a tip of the elongate electrode rod on a downstream side of the plasma output hole, the first portion of the elongate electrode rod having a uniform cross section.

2. The hybrid plasma device for skin beauty and skin regeneration treatments of claim 1, wherein the gas supply unit includes:

a first inert gas tank configured to supply nitrogen; and a second inert gas tank configured to supply argon.

3. The hybrid plasma device for skin beauty and skin regeneration treatments of claim 1, wherein the gas output unit includes:

output regulators configured to mix two or more species of the inert gases supplied from the gas supply unit so as to generate a mixed inert gas;

a pneumatic sensor configured to sense a pressure state of the mixed inert gas from the output regulators; and a pneumatic solenoid valve configured to regulate a pressure of the mixed inert gas output to the plasma handpiece based on the skin treatment program input from the manipulation unit, wherein the control unit is configured to control the gas output unit, based on the at least two skin treatment programs, to output one species of inert gas or a mixture of two or more species of inert gases to the plasma handpiece.

4. The hybrid plasma device for skin beauty and skin regeneration treatments of claim 1, wherein the plurality of skin treatment programs includes a skin beauty treatment program and a skin regeneration treatment program, wherein a mixture ratio of inert gases for the skin beauty treatment program is different from a mixture ratio of inert gases for the skin regeneration treatment program.

\* \* \* \* \*